United States Patent
Grazioso et al.

(10) Patent No.: US 9,588,230 B2
(45) Date of Patent: Mar. 7, 2017

(54) SYSTEMS AND METHODS FOR CALIBRATING A SILICON PHOTOMULTIPLIER-BASED POSITRON EMISSION TOMOGRAPHY SYSTEM

(75) Inventors: Ronald Grazioso, Knoxville, TN (US); Debora Henseler, Erlangen (DE); Nan Zhang, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2203 days.

(21) Appl. No.: 12/560,054

(22) Filed: Sep. 15, 2009

(65) Prior Publication Data

US 2010/0065746 A1 Mar. 18, 2010

Related U.S. Application Data

(60) Provisional application No. 61/096,951, filed on Sep. 15, 2008.

(51) Int. Cl.
*G01D 18/00* (2006.01)
*G12B 13/00* (2006.01)
*G01T 1/164* (2006.01)
*A61B 6/03* (2006.01)

(52) U.S. Cl.
CPC .......... *G01T 1/1644* (2013.01); *G01T 1/1648* (2013.01); *A61B 6/037* (2013.01)

(58) Field of Classification Search
USPC .......................................... 250/252.1, 363.03
See application file for complete search history.

(56) References Cited

U.S. PATENT DOCUMENTS

| 7,071,474 B2 * | 7/2006 | Wong et al. ............. 250/363.09 |
| 7,157,681 B1 * | 1/2007 | Tetzlaff ......................... 250/207 |
| 8,046,601 B1 * | 10/2011 | Paz et al. ...................... 713/300 |
| 2010/0176301 A1 * | 7/2010 | Wieczorek et al. ..... 250/363.02 |

* cited by examiner

*Primary Examiner* — David Porta
*Assistant Examiner* — Carolyn Igyarto

(57) ABSTRACT

A representative positron emission tomography (PET) system includes a positron emission tomography detector having one or more silicon photomultipliers that output silicon photomultipliers signals. The PET system further includes a calibration system that is electrically coupled to the silicon photomultipliers. The calibration system determines a single photoelectron response of the silicon photomultipliers signals and adjusts a gain of the silicon photomultipliers based on the single photoelectron response.

27 Claims, 4 Drawing Sheets

SYSTEMS AND METHODS FOR CALIBRATING A SILICON PHOTOMULTIPLIER-BASED POSITRON EMISSION TOMOGRAPHY SYSTEM

CROSS-REFERENCE TO RELATED APPLICATIONS

This application claims the benefit of U.S. provisional patent application Ser. No. 61/096,951 filed Sep. 15, 2008, the entirety of which application is expressly incorporated by reference herein.

TECHNICAL FIELD

The present disclosure is generally related to nuclear medical imaging and, more particularly, is related to systems and methods for calibrating a silicon photomultiplier-based positron emission tomography system.

BACKGROUND

Typically, in commercial photomultiplier tube-based positron emission tomography systems, a potentiometer is adjusted so that each photomultiplier tube signal amplitude is identical within the scanner or at least for each block detector. A scintillator array or light pulser is optically coupled to the photomultiplier tubes and the light pulses are used to adjust each photomultiplier tube in a positron emission tomography system. This is not very exact since the light pulses may not have the same exact light output; therefore, the gain adjustment is based on an average of light pulse outputs. This procedure is usually done by hand, by a trained technician, using a voltage potentiometer attached to the voltage circuit.

Desirable in the art is an improved photosensor and a calibration system that would improve upon the conventional PET systems.

SUMMARY

A representative positron emission tomography (PET) system includes a positron emission tomography detector having one or more silicon photomultipliers that output silicon photomultiplier signals. The PET system further includes a calibration system that is electrically coupled to the silicon photomultipliers. The calibration system determines a single photoelectron response of the silicon photomultiplier signals and adjusts a gain of the silicon photomultipliers based on the single photoelectron response.

Other systems, devices, methods, features of the present disclosure will be or will become apparent to one skilled in the art upon examination of the following figures and detailed description. It is intended that all such systems, devices, methods, features be included within the scope of the present disclosure, and be protected by the accompanying claims.

BRIEF DESCRIPTION OF DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, the reference numerals designate corresponding parts throughout the several views. While several embodiments are described in connection with these drawings, there is no intent to limit the disclosure to the embodiment or embodiments disclosed herein. On the contrary, the intent is to cover all alternatives, modifications, and equivalents.

DETAILED DESCRIPTION

Exemplary systems are first discussed with reference to the figures. Although these systems are described in detail, they are provided for purposes of illustration only and various modifications are feasible. After the exemplary systems are described, examples of flow diagrams of the systems are provided to explain the manner in which a silicon photomultiplier-based positron emission tomography system can be calibrated.

Figure 1:
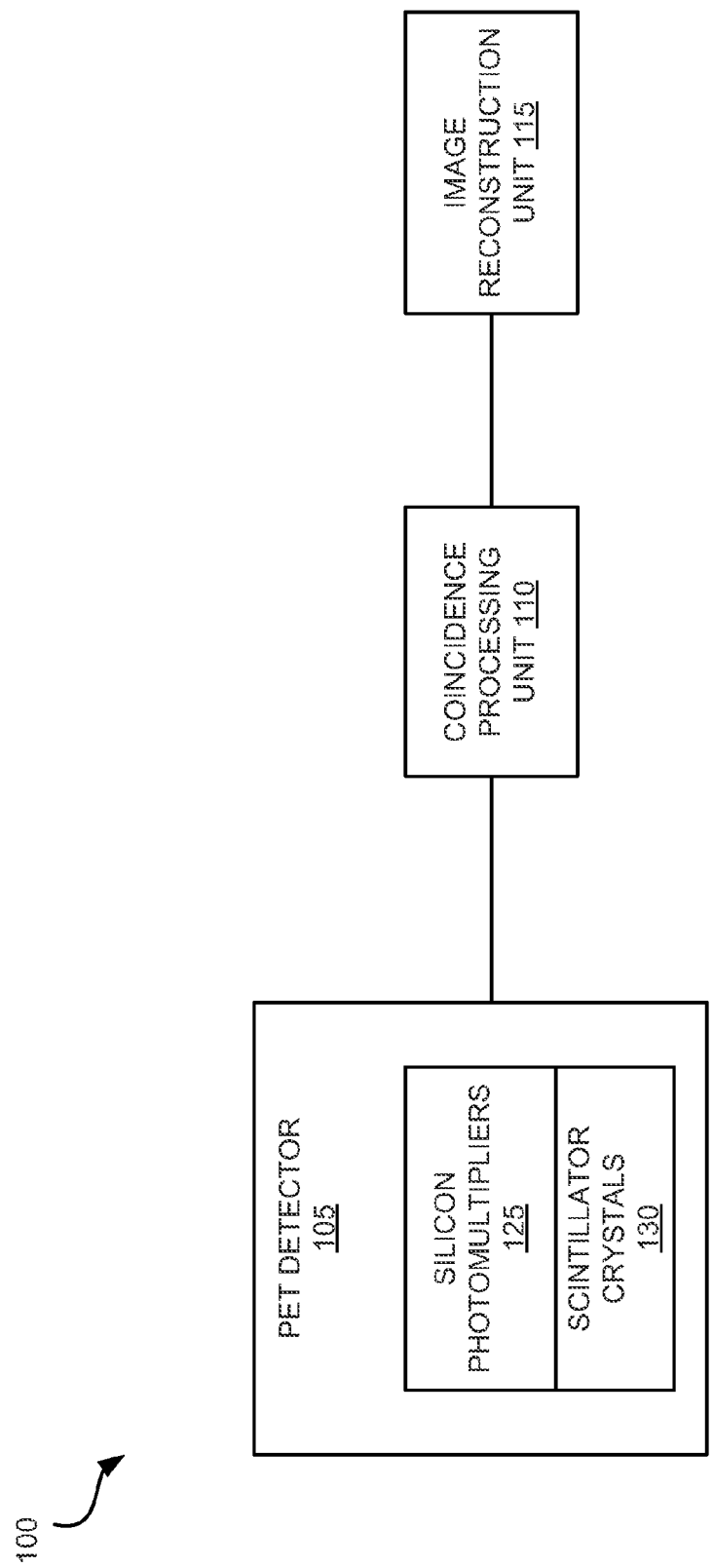
FIG. 1 is a high-level block diagram of a positron emission tomography system having silicon photomultipliers in accordance with an embodiment of the present disclosure.

FIG. 1 is a high-level block diagram of a positron emission tomography system 100 having silicon photomultipliers 125 in accordance with an embodiment of the present disclosure. The positron emission tomography system 100 includes a positron emission tomography detector 105 having scintillator crystals 130 and silicon photomultipliers 125. In general, a living subject is injected with a short-lived radioactive tracer isotope (e.g., usually into blood circulation) before conducting a positron emission tomography scan. The tracer isotope is for example fluorodeoxyglucose (FDG), which is a type of sugar. During the positron emission tomography scan, data is recorded from the tracer-concentrated tissue as the tracer isotope decays.

As the tracer-concentrated tissue undergoes positron emission decay, the tissue emits a positron, which is an antiparticle of the electron with opposite charge. The positron eventually collides with an electron, producing a pair of annihilation (gamma) photons moving in opposite directions. The gamma photons are detected when they reach the scintillator crystals 130 in the positron emission tomography detector 105, creating a burst of light which is detected by the silicon photomultipliers 125. The pair of photons move in approximately opposite directions and are processed to determine whether the detected pair of photons are a coincidence event by the coincidence processing unit 110. If so, positional data for the pair of photons are sent to the image reconstruction unit 115 for producing an image that is generated using mathematical image reconstruction procedures.

Figure 2:
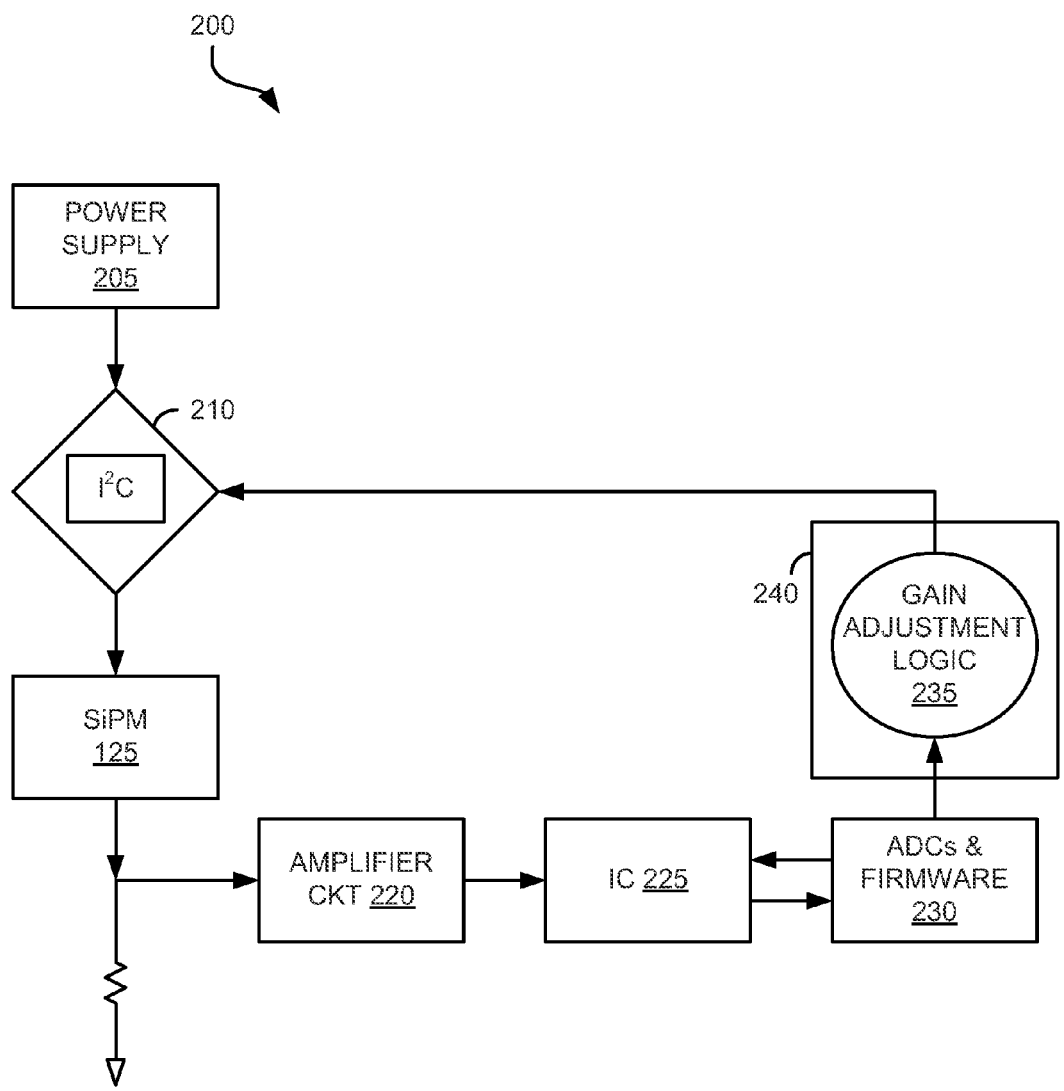
FIG. 2 is a detailed block diagram of a silicon photomultiplier-based positron emission tomography calibration system in accordance with an embodiment of the present disclosure.

The silicon photomultipliers 125 are silicon photosensors that work on the principle of a Geiger-mode avalanche photodiode. The silicon photomultiplier 125 is generally an array of Geiger-mode avalanche photodiodes connected together via a network of resistors. The silicon photomultipliers 125 have high gain, low noise and good single photoelectron (s.p.e.) detection. However, the silicon photomultipliers 125 can be very sensitive to voltage and temperature fluctuations. Referring to FIG. 2 with a calibration system 200 (FIG. 2), the gain of the silicon photomultipliers 125 can be adjusted so that each silicon photomultiplier 125 can operate at or about the same gain within the positron emission tomography system 100. The calibration system 200 is further described in connection with FIGS. 2 and 3.

FIG. 2 is a detailed block diagram of a silicon photomultiplier-based positron emission tomography calibration system 200 in accordance with a preferred embodiment of the present disclosure. The silicon photomultiplier-based positron emission tomography calibration system 200 includes a power supply 205 that is electrically coupled to an inter-integrated circuit 210 that facilitates adjusting the operating voltage of the silicon photomultipliers 125. For example, Hamamatsu silicon photomultipliers have an operating range of 60V to 80V. The inter-integrated circuit (I2C) 210 can facilitate operating the Hamamatsu silicon photomultipliers starting at, e.g., 77.0V, and increasing the operating voltage by a tenth of a volt for achieving acceptable calibration criteria. The inter-integrated circuit 210 is electrically coupled to the silicon photomultipliers 125, which detect coincidence events and output a signal. In addition to the signals from the coincidence events, the silicon photomultipliers 125 also output dark signals. The dark signals can have the amplitudes of single photoelectron (s.p.e.) signals or multiples of the s.p.e. signals.

The amplifier circuit 220 receives and amplifies the silicon photomultiplier signal for an integrated circuit 225, e.g., an application-specific integrated circuit (ASIC), which is electrically coupled to the analog-to-digital converter (ADC) and firmware 230. Both the integrated circuit 225 and ADC/firmware 230 process the amplified silicon photomultiplier signals and the ADC/firmware 230 sends the processed silicon photomultiplier signals to a gain adjustment logic 235, which can be stored in memory 240 of the positron emission tomography system 100. The gain adjustment logic 235 determines whether to increase or decrease the operating voltage of the silicon photomultipliers 125 based on the processed silicon photomultiplier signals, after identifying the single photoelectron peak from a series of silicon photomultiplier dark measurements. The gain adjustment logic 235 instructs the inter-integrated circuit 210 to adjust the operating voltage of the silicon photomultipliers 125.

Figure 3:
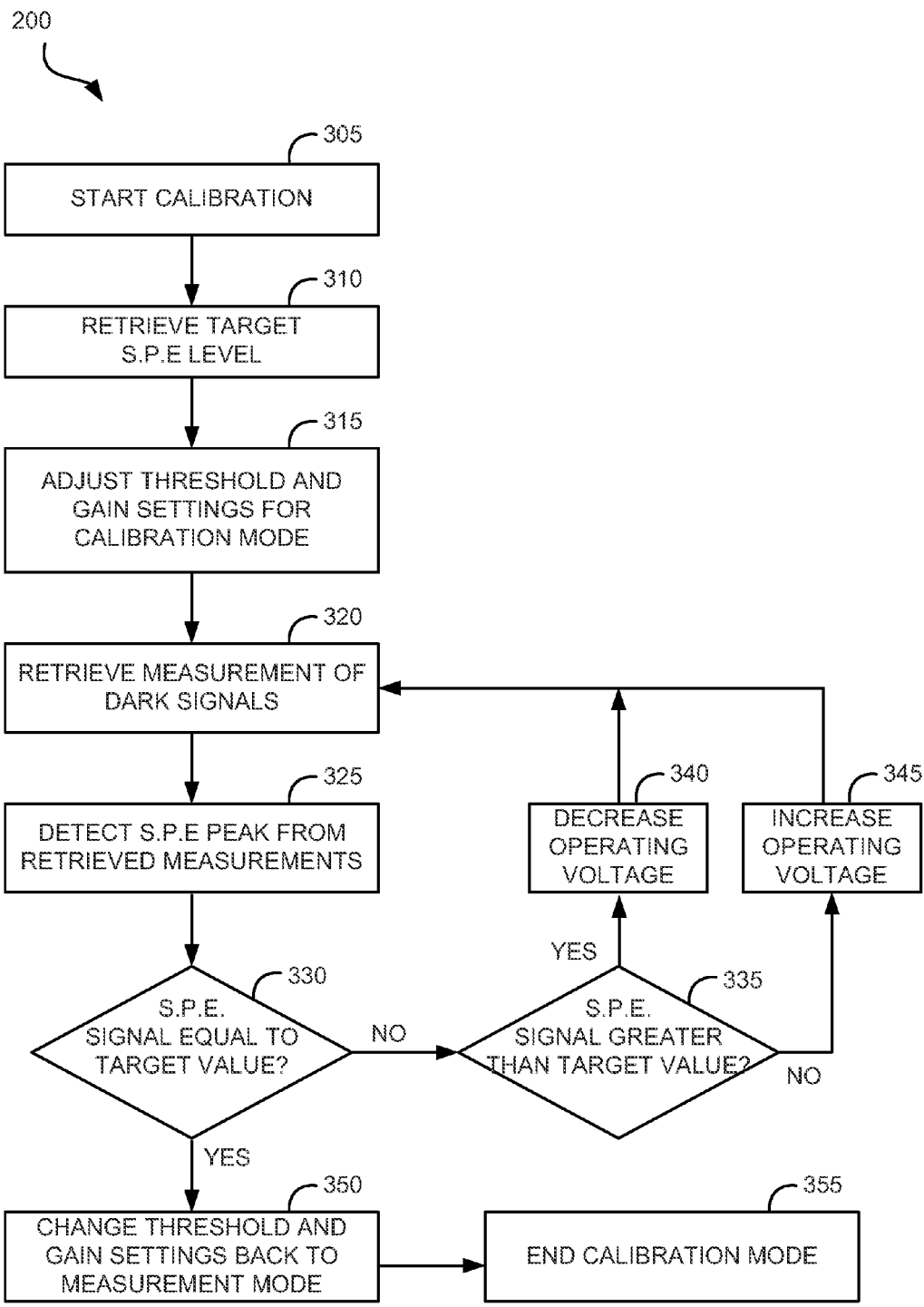
FIG. 3 is a flow diagram that illustrates an embodiment of the architecture, functionality, and/or operation of a silicon photomultiplier-based positron emission tomography calibration system in accordance with an embodiment of the present disclosure.

FIG. 3 is a flow diagram that illustrates an embodiment of the architecture, functionality, and/or operation of a silicon photomultiplier-based positron emission tomography calibration system 200 in accordance with an implementation of the present disclosure. Beginning with steps 305 and 310, the calibration system 200 starts the calibration mode and the gain adjustment logic 235 retrieves a target single photoelectron level, respectively. The target signal photoelectron level is a reference value that can be obtained from a table map stored in memory 240 or inputted by a user via a user interface (not shown). In steps 315 and 320, the gain adjustment logic 235 adjusts the threshold and gain settings of the amplifier circuit 220 for the calibration mode and retrieves the measurements of several dark signals from the silicon photomultipliers 125, respectively.

Figure 4:
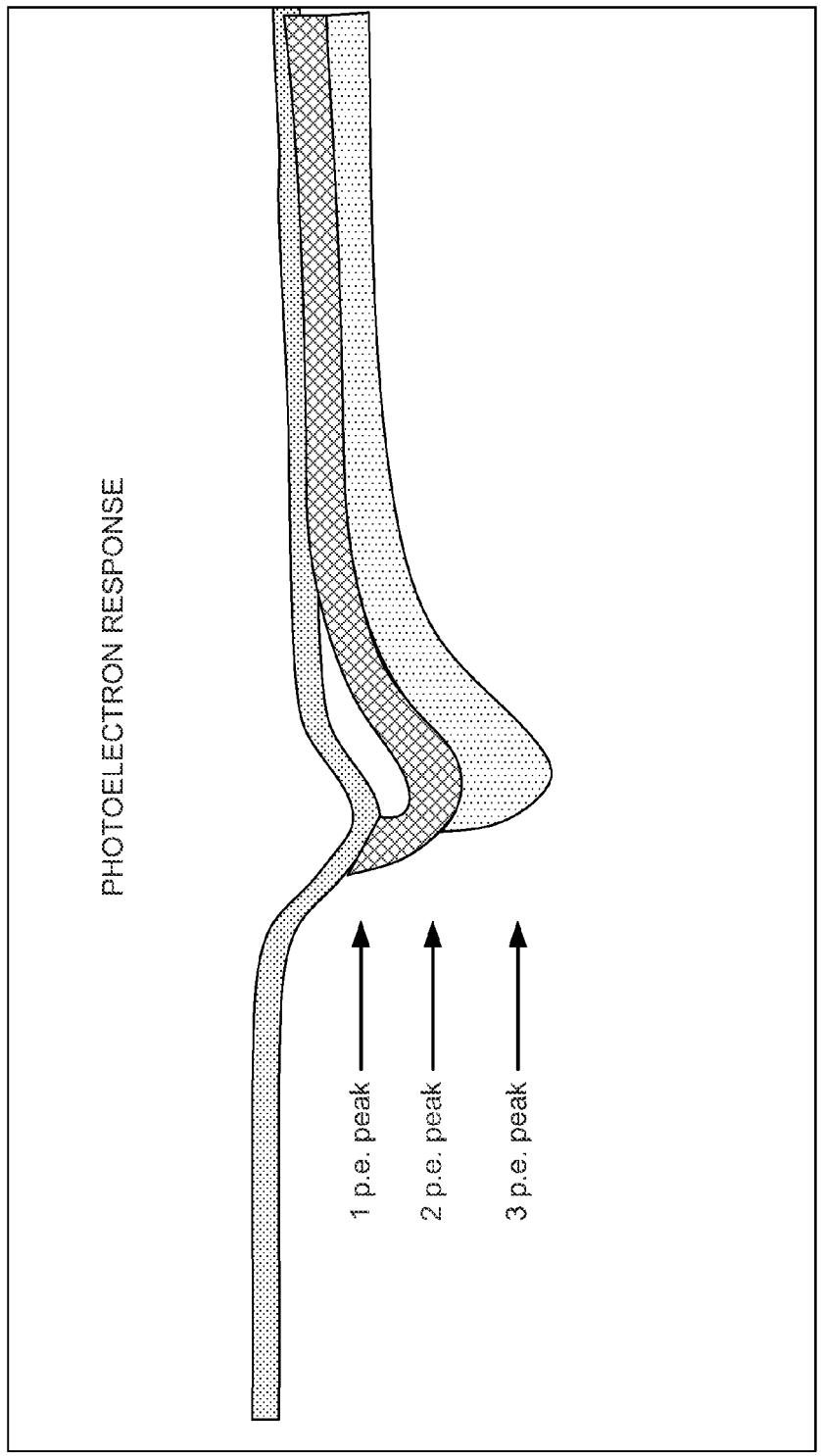
FIG. 4 is an image showing an exemplary single photoelectron response showing 1, 2, and 3 photoelectron peaks.

In step 325, the gain adjustment logic 235 detects the single photoelectron peak from a series of retrieved measurements. The detected single photoelectron peak can be compared with a reference peak of a photoelectron response spectrum, such as that shown in FIG. 4. The amplitude of a 1 photoelectron peak in FIG. 4 can be, for example, approximately 152 mV. In step 330, the gain adjustment logic 235 determines whether the single photoelectron peak is equal to a target value (or within a pre-defined boundary of the target value). If so, the gain adjustment logic 235 in steps 350 and 355 changes the threshold and gain settings of the amplifier circuit 220 back to the measurement mode and ends the calibration mode, respectively. For example, the target value can be an average of single photoelectron peaks from several tested silicon photomultipliers.

If the single photoelectron peak is not equal to the target value, the gain adjustment logic 235 in step 335 determines whether the single photoelectron peak is greater than the target value. Responsive to determining that the single photoelectron peak is greater than the target value, the gain adjustment logic 235 in step 340 instructs the inter-integrated circuit 210 to decrease the operating voltage of the silicon photomultipliers 125 by a pre-defined increment. Responsive to determining that the single photoelectron peak is lesser than the target value, the gain adjustment logic 235 in step 345 instructs the inter-integrated circuit 210 to increase the operating voltage of the silicon photomultipliers 125 by a pre-defined increment. The calibration system 200 can repeat steps 320, 325, 330, 335, 340, and 345 until the single photoelectron peak is equal to the target value.

It should be noted that any process descriptions or blocks in flowcharts should be understood as representing modules, segments, or portions of code which include one or more executable instructions for implementing specific logical functions or steps in the process. As would be understood by those of ordinary skill in the art of the software development, alternate embodiments are also included within the scope of the disclosure. In these alternate embodiments, functions may be executed out of order from that shown or discussed, including substantially concurrently or in reverse order, depending on the functionality involved.

The systems and methods disclosed herein can be implemented in software, hardware, or a combination thereof. In some embodiments, the system and/or method is implemented in software that is stored in a memory and that is executed by a suitable microprocessor (μP) situated in a computing device. However, the systems and methods can be embodied in any computer-readable medium for use by or in connection with an instruction execution system, apparatus, or device. Such instruction execution systems include any computer-based system, processor-containing system, or other system that can fetch and execute the instructions from the instruction execution system. In the context of this disclosure, a "computer-readable medium" can be any means that can contain, store, communicate, propagate, or transport the program for use by, or in connection with, the instruction execution system. The computer readable medium can be, for example, but not limited to, a system or propagation medium that is based on electronic, magnetic, optical, electromagnetic, infrared, or semiconductor technology.

Specific examples of a computer-readable medium using electronic technology would include (but are not limited to) the following: an electrical connection (electronic) having one or more wires; a random access memory (RAM); a read-only memory (ROM); an erasable programmable read-only memory (EPROM or Flash memory). A specific example using magnetic technology includes (but is not limited to) a portable computer diskette. Specific examples using optical technology include (but are not limited to) optical fiber and compact disc read-only memory (CD-ROM).

Note that the computer-readable medium could even be paper or another suitable medium on which the program is printed. Using such a medium, the program can be electronically captured (using, for instance, optical scanning of the paper or other medium), compiled, interpreted or otherwise processed in a suitable manner, and then stored in a computer memory. In addition, the scope of the certain embodiments of the present disclosure includes embodying the functionality of the preferred embodiments of the present disclosure in logic embodied in hardware or software-configured mediums.

This description has been presented for purposes of illustration and description. It is not intended to be exhaustive or to limit the disclosure to the precise forms disclosed. Obvious modifications or variations are possible in light of the above teachings. The embodiments discussed, however, were chosen to illustrate the principles of the disclosure, and its practical application. The disclosure is thus intended to enable one of ordinary skill in the art to use the disclosure, in various embodiments and with various modifications, as are suited to the particular use contemplated. All such modifications and variation are within the scope of this disclosure, as determined by the appended claims when interpreted in accordance with the breadth to which they are fairly and legally entitled.

Therefore, having thus described the disclosure, at least the following is claimed:

1. A positron emission tomography calibration system comprising:
    an array of silicon photomultipliers responsive to incident single photoelectrons to output silicon photomultiplier signals; and
    a gain adjustment logic receiving said silicon photomultiplier signals, determining a single photoelectron response of the silicon photomultipliers based on said silicon photomultiplier signals, comparing the single photoelectron response with a target value, and adjusting a gain of the silicon photomultipliers based on a result of the comparison.

2. The positron emission tomography calibration system of claim 1, further comprising an amplifier circuit that amplifies said silicon photomultiplier signals in accordance with threshold and gain settings, wherein the gain adjustment logic adjusts the threshold and gain settings of the amplifier circuit in a calibration mode for calibrating said gain of said silicon photomultipliers.

3. The positron emission tomography calibration system of claim 1, further comprising an inter-integrated circuit that facilitates adjusting an operating voltage of the silicon photomultipliers.

4. The positron emission tomography calibration system of claim 1, wherein the gain adjustment logic determines whether to increase or decrease an operating voltage of the silicon photomultipliers based on the result of said comparison.

5. The positron emission tomography calibration system of claim 4, wherein the gain adjustment logic determines whether a peak of said single photoelectron response is equal to a target value.

6. The positron emission tomography calibration system of claim 5, further comprising an inter-integrated circuit that facilitates adjusting an operating voltage of the silicon photomultipliers, wherein the gain adjustment logic instructs the inter-integrated circuit to decrease or increase the operating voltage of the silicon photomultipliers by a pre-defined increment responsive to determining whether the single photoelectron peak is greater or lesser than a target value.

7. The positron emission tomography calibration system of claim 1, further comprising an integrated circuit, an analog-to-digital converter and a firmware, which process the silicon photomultiplier signals for the gain adjustment logic.

8. A positron emission tomography system comprising:
    a positron emission tomography detector having an array of silicon photomultipliers that output silicon photomultiplier signals in response to incident single photoelectrons; and
    a calibration system that is electrically coupled to the silicon photomultipliers, wherein the calibration system determines a single photoelectron response of the array of silicon photomultipliers based on said signals, and adjusts a gain of the silicon photomultipliers based on a comparison of the single photoelectron response with a target value.

9. The positron emission tomography system of claim 8, wherein the single photoelectron response is determined from dark signals that have amplitudes of single photoelectron (s.p.e.) signals or multiples of the s.p.e. signals.

10. The positron emission tomography system of claim 9, wherein the calibration system includes a gain adjustment logic that determines whether to increase or decrease an operating voltage of the silicon photomultipliers based on the result of said comparison.

11. The positron emission tomography system of claim 10, wherein the gain adjustment logic identifies a single photoelectron peak single photoelectron peak.

12. The positron emission tomography system of claim 10, wherein the calibration system includes an inter-integrated circuit that facilitates adjusting the operating voltage of the silicon photomultipliers.

13. The positron emission tomography system of claim 11, wherein the gain adjustment logic determines whether the single photoelectron peak is equal to a target value.

14. The positron emission tomography system of claim 13, wherein the calibration system includes an inter-integrated circuit that facilitates adjusting the operating voltage of the silicon photomultipliers, and wherein the gain adjustment logic instructs the inter-integrated circuit to decrease or increase the operating voltage of the silicon photomultipliers by a pre-defined increment responsive to determining whether the single photoelectron peak is greater or lesser than a target value.

15. The positron emission tomography system of claim 10, wherein the calibration system includes an amplifier circuit that amplifies said silicon photomultiplier signals in accordance with threshold and gain settings, wherein the gain adjustment logic adjusts the threshold and gain settings of the amplifier circuit in a calibration mode for calibrating said gain of said silicon photomultipliers.

16. A method for calibrating a silicon photomultiplier-based positron emission tomography system comprising:
    detecting a single photoelectron peak from silicon photomultiplier signals of an array of silicon photomultipliers in response to incident single photoelectrons;
    comparing the single photoelectron peak is equal to a target value; and
    adjusting a gain of the silicon photomultipliers based on a result of said comparing.

17. The method of claim 16, wherein said target value is a target single photoelectron level that is obtained from a table map stored in memory or inputted by a user via a user interface.

18. The method of claim 16, further comprising adjusting threshold and gain settings of an amplifier circuit to set up the silicon photomultiplier-based positron emission tomography system for a calibration mode and retrieving measurements of several dark signals from the silicon photomultipliers in said calibration mode.

19. The method of claim 18, wherein the single photoelectron peak is detected from a series of retrieved measurements, wherein the detected single photoelectron peak is compared with a reference peak of a photoelectron response spectrum.

20. The method of claim 16, further comprising decreasing an operating voltage of the silicon photomultipliers responsive to determining that the single photoelectron peak is greater than the target value.

21. The method of claim 16, further comprising increasing an operating voltage of the silicon photomultipliers responsive to determining that the single photoelectron peak is lesser than the target value.

22. A positron emission tomography calibration system comprising:
   a processing device; and
   a non-transitory computer-readable medium storing computer-executable instructions that are executable by the processing device, which instructions cause the processing device to
      detect a single photoelectron peak from silicon photomultiplier signals of an array of silicon photomultipliers in response to incident single photoelectrons;
      compare the single photoelectron peak with a target value; and
      adjust a gain of the silicon photomultipliers based on a result of the comparison.

23. The positron emission tomography calibration system of claim 22, wherein the instructions further include instructions causing said processing device to retrieve as said target value a target single photoelectron level from a table map stored in memory or inputted by a user via a user interface.

24. The positron emission tomography calibration system of claim 22, wherein the instructions further include instructions causing said processing device to adjust threshold and gain settings of an amplifier circuit to set up the silicon photomultiplier-based positron emission tomography system for a calibration mode and retrieving measurements of several dark signals from the silicon photomultipliers in said calibration mode.

25. The positron emission tomography calibration system of claim 24, wherein the single photoelectron peak is detected from a series of retrieved measurements, wherein the detected single photoelectron peak is compared with a reference peak of a photoelectron response spectrum.

26. The positron emission tomography calibration system of claim 22, wherein the instructions further include instructions for causing said processing device to decrease decreasing an operating voltage of the silicon photomultipliers responsive to determining that the single photoelectron peak is greater than the target value.

27. The positron emission tomography calibration system of claim 22, wherein the instructions further include instructions for causing said processing device to increase an operating voltage of the silicon photomultipliers responsive to determining that the single photoelectron peak is lesser than the target value.

* * * * *